United States Patent [19]

Jacob et al.

[11] Patent Number: 4,747,829
[45] Date of Patent: May 31, 1988

[54] PRE-FILLED SYRINGE

[75] Inventors: Jean-Louis Jacob; Gaetan Sanschagrin; Jean Thibodeau; France Guay, all of Quebec, Canada

[73] Assignee: E. R. Squibb & Sons, Inc., Princeton, N.J.

[21] Appl. No.: 5,717

[22] Filed: Jan. 21, 1987

[51] Int. Cl.⁴ .............................................. A61M 5/32
[52] U.S. Cl. ..................................... 604/110; 604/198
[58] Field of Search ............... 604/110, 111, 194, 195, 604/196, 197, 198, 220, 228

[56] References Cited

U.S. PATENT DOCUMENTS

| | | |
|---|---|---|
| 2,153,594 | 4/1939 | Saffir . |
| 2,408,323 | 9/1946 | Lockhart . |
| 2,453,591 | 11/1943 | Doux . |
| 2,489,600 | 11/1949 | Tydings et al. . |
| 2,841,144 | 7/1958 | Cohen et al. . |
| 3,108,591 | 10/1963 | Kolbas . |
| 3,182,660 | 5/1965 | Weydanz et al. . |
| 3,368,558 | 2/1968 | Sarnoff et al. . |
| 3,406,686 | 10/1968 | Keller . |
| 3,524,445 | 8/1970 | Frieze . |
| 3,724,460 | 4/1973 | Gomez et al. . |
| 3,735,761 | 5/1973 | Hurschman et al. . |
| 3,811,441 | 5/1974 | Sarnoff . |
| 3,941,131 | 4/1976 | Ogle . |
| 3,946,732 | 4/1976 | Hurscham . |
| 4,026,287 | 5/1977 | Haller .............................. 604/195 X |
| 4,036,225 | 7/1977 | Maury . |
| 4,171,698 | 10/1979 | Genese . |
| 4,392,859 | 7/1983 | Dent . |
| 4,405,317 | 9/1983 | Case . |
| 4,474,734 | 10/1984 | Cooper . |
| 4,475,906 | 10/1984 | Holzner . |
| 4,482,348 | 11/1984 | Dent . |
| 4,507,117 | 3/1985 | Vining et al. ........................ 604/196 |
| 4,507,118 | 3/1985 | Dent . |
| 4,592,744 | 6/1986 | Jagger et al. ........................ 604/197 |
| 4,613,326 | 9/1986 | Szare . |
| 4,675,005 | 6/1987 | Deluccia ............................ 604/110 |

FOREIGN PATENT DOCUMENTS

| | | |
|---|---|---|
| 742024 | 9/1966 | Canada . |
| 864276 | 2/1971 | Canada . |
| 912389 | 10/1972 | Canada . |
| 945029 | 4/1974 | Canada . |
| 1001032 | 12/1976 | Canada . |
| 1015237 | 3/1977 | Canada . |
| 1016436 | 8/1977 | Canada . |
| 1058035 | 7/1979 | Canada . |
| 1093409 | 1/1981 | Canada . |
| 1136505 | 11/1982 | Canada . |
| 1144838 | 4/1983 | Canada . |
| 1147627 | 6/1983 | Canada . |
| 1185858 | 4/1985 | Canada . |
| 8300109 | 10/1983 | PCT Int'l Appl. . |

Primary Examiner—John D. Yasko
Attorney, Agent, or Firm—Lawrence S. Levinson; Robert E. Lee, Jr.

[57] ABSTRACT

A pre-filled syringe is provided with a retractile needle. The needle end of a syringe is enclosed in a sterile chamber within a casing sealed by a cap with a break-off tip. The barrel of the syringe is movable within the casing from a remote pre-injection position to a forward injection position and back again. When the barrel is moved forward a first end of the needle passes through the opening of the cap and then the opposite end comes in contact with the injectant. When the barrel is withdrawn to a pre-injection position, the needle is retracted within the casing and is prevented from re-entering the opening in the cap.

30 Claims, 10 Drawing Sheets

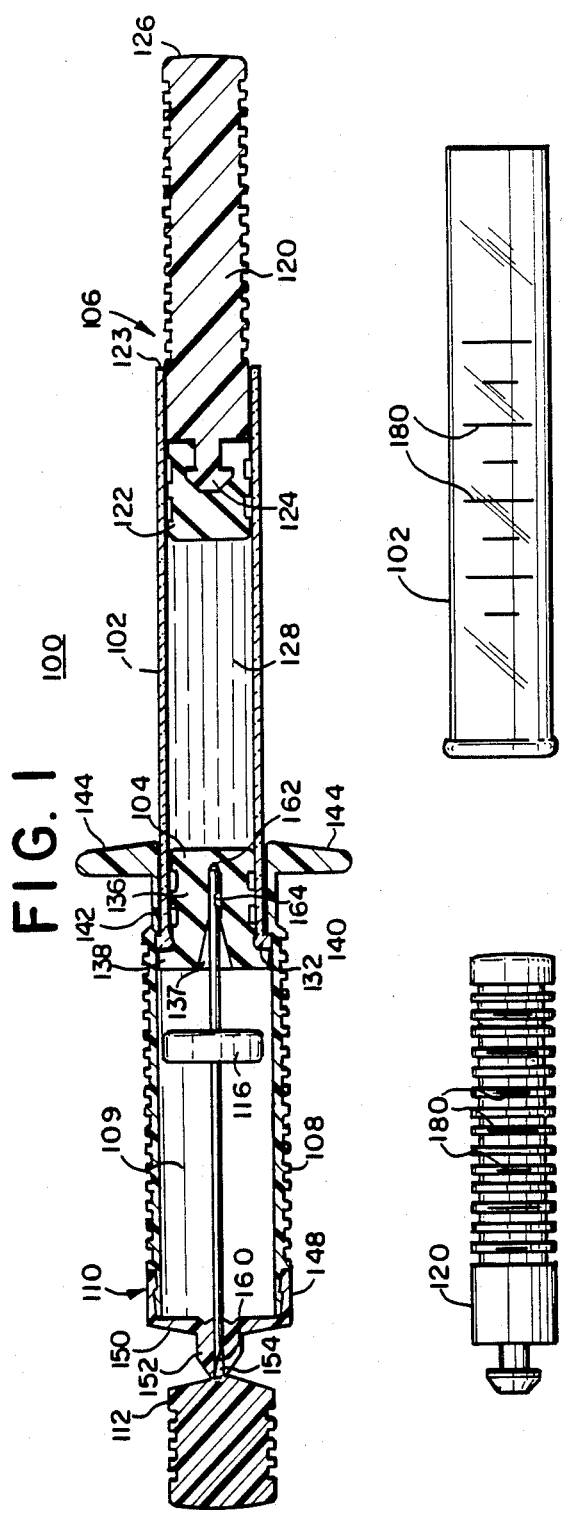

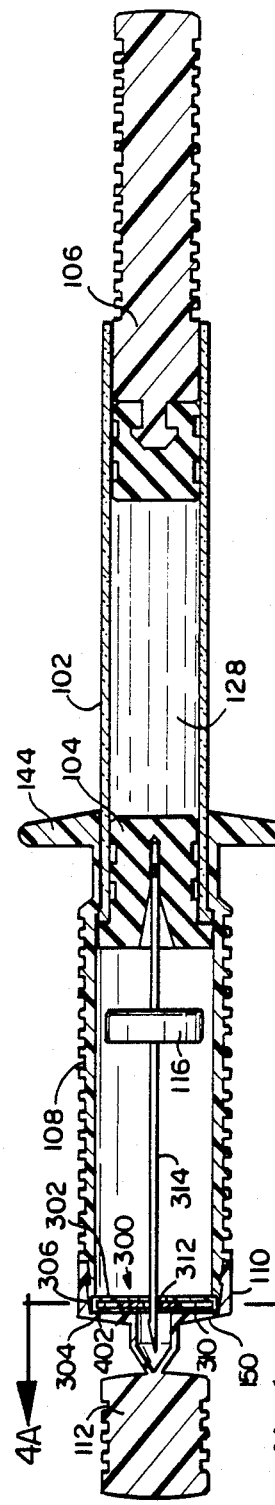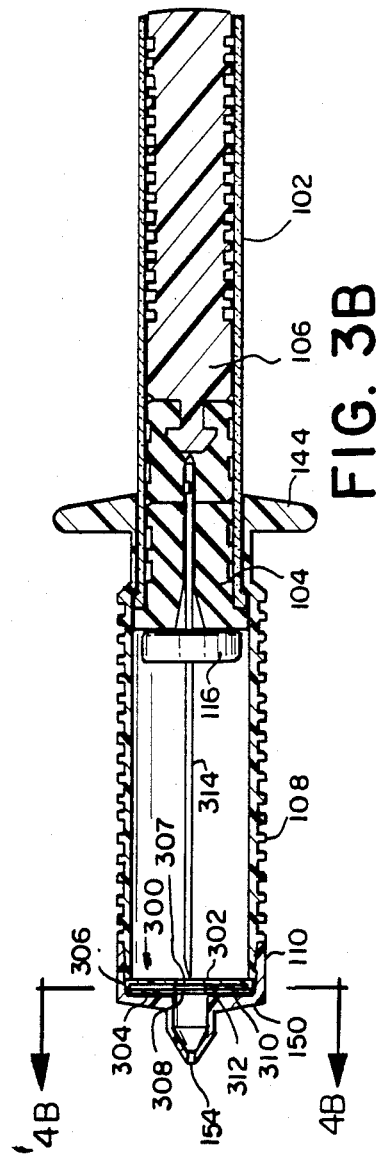
FIG. 3A
FIG. 3B

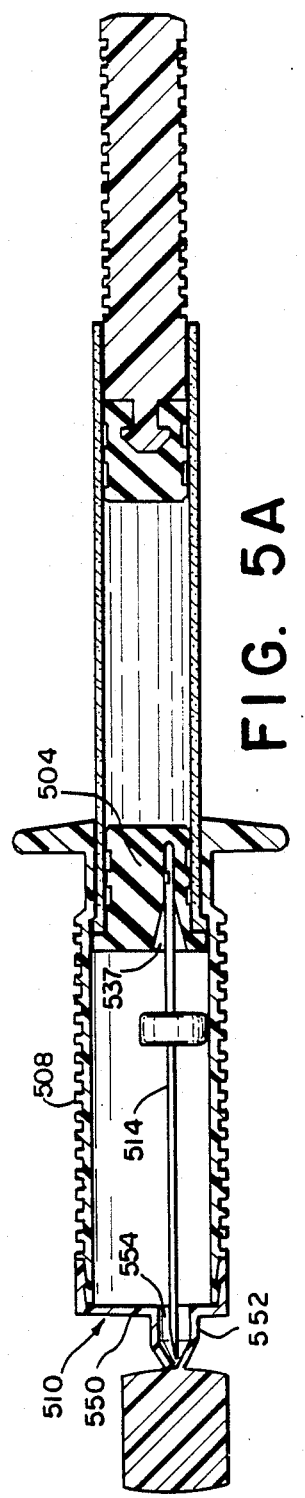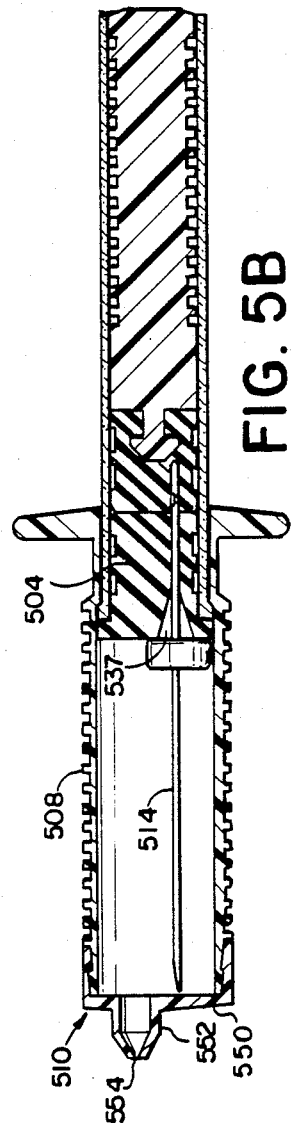

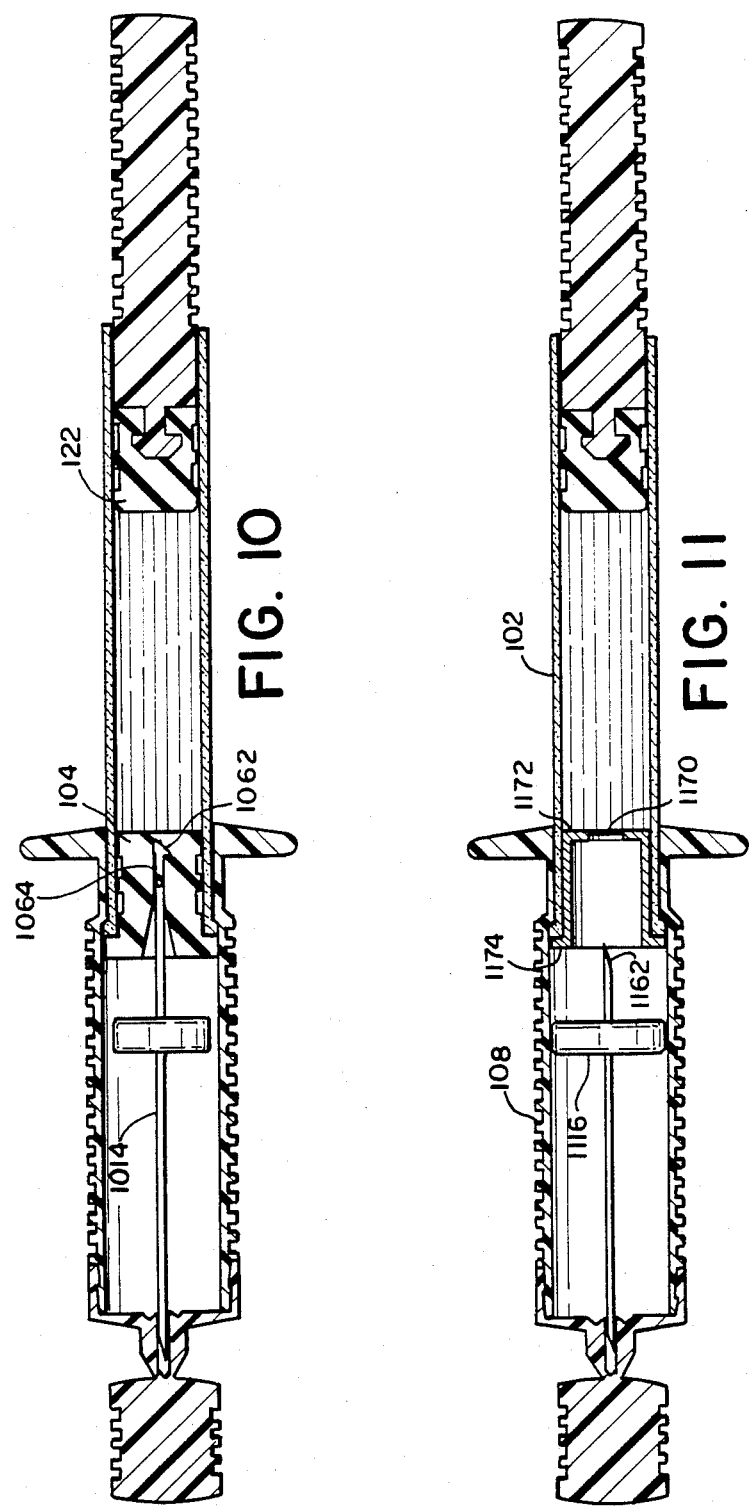

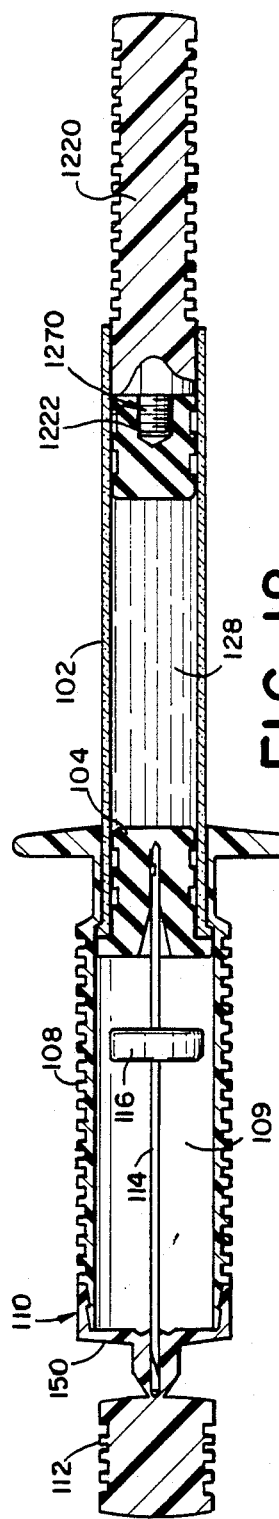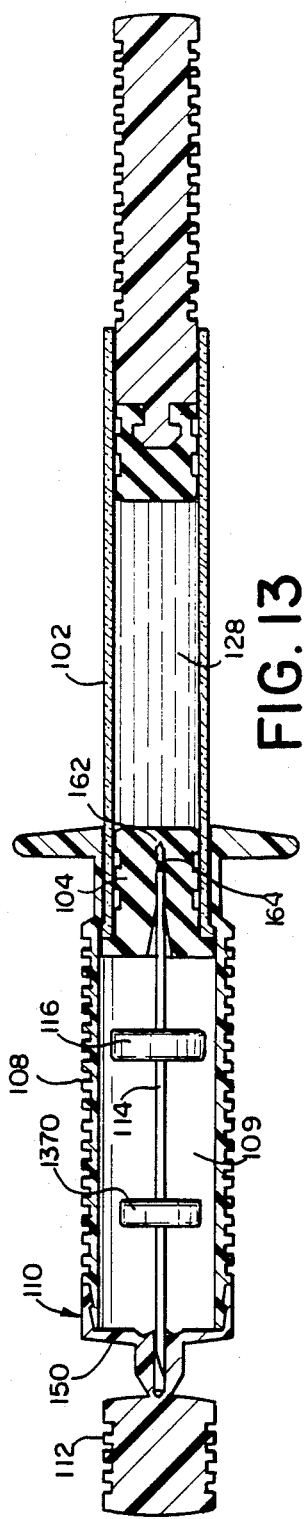

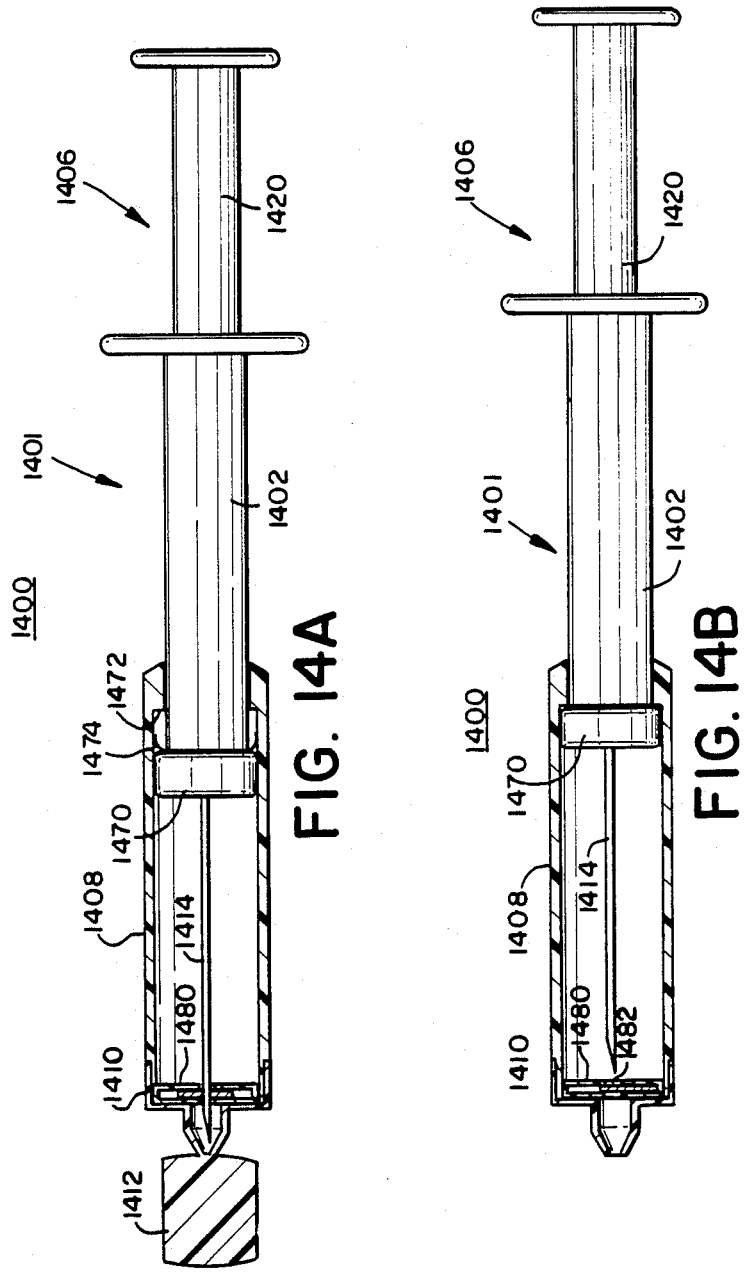

PRE-FILLED SYRINGE

BACKGROUND OF THE INVENTION

The present invention relates to a pre-filled syringe with a retractile needle more particularly, to a syringe intended for a single use. Many prior art syringes have a fixed needle which is capped or sealed in a plastic wrap but which is otherwise exposed and susceptible to breakage. After a syringe has been used there is often a danger associated with the exposed needle of a used syringe which may not have been safely and immediately discarded. For example, with the threat of the AIDS disease a needle which comes in contact with a patient's blood and is then discarded might infect someone who later comes in contact with the exposed needle of the syringe. There is also some danger that someone may attempt to reuse the now non-sterile syringe.

It is desirable therefore to provide for a pre-filled, easily assembled syringe which is unusable and whose needle is inaccessible after its intended one time use.

SUMMARY OF THE INVENTION

The present invention relates to an improved syringe which is easy to manufacture and package and safer to use. It comprises a barrel for holding an injectant and a plunger adapted for sliding engagement with the interior of the barrel through one end thereof to eject the injectant. In the preferred embodiment, the plunger, once fully inserted in the barrel, is difficult to remove thus helping to prevent re-use.

The improved syringe further includes a hollow casing coupled to the end of the barrel opposite the plunger. The barrel is free to move from a remote pre-injection position to a forward injection position and back again. In the preferred embodiment, the end of the casing opposite the barrel is closed by a cap with a break-off tip, the cap including a channel supporting the tip of the needle. The channel opens at one end to the interior of the casing and extends to the opposite end of the protrusion at the tip, thereby creating a weakness between the protrusion and the break off tip.

A hollow needle, provided within the casing, is initially aligned with the channel of the cap and is supported by a stopper inserted in the barrel at the end opposite the plunger. In the preferred embodiment, the end of the needle rests within a channel in the stopper closed at one end. The needle is prevented from coming in contact with the injectant by the closed end of the channel of the stopper. A stop cock is fixed to the needle within the casing at a predetermined distance from the stopper.

To operate the syringe, the break off tip is removed, the barrel is inserted fully into the casing and the plunger is pushed completely into the barrel to eject the injectant. When the barrel is inserted into the casing, the needle moves through the channel of the cap until the stop cock engages the inside wall of the cap. The barrel will move forward until the stopper engages the stop cock forcing the end of the needle through the stopper into the injectant. In the preferred embodiment, a hole is provided on the side of the needle, spaced apart from the tip of the needle which comes in contact with the injectant. This helps to reduce the number of rubber fragments getting into the needle as it passes through the stopper.

When the injection is complete the barrel is withdrawn from the casing to the pre-injection position. In the preferred embodiment the needle is pre-stressed and initially one end is positioned within the channel of the cap. After injection, the length of the needle extending forward of the stopper is shortened because a portion of the needle passes through the stopper as described above. When the barrel is withdrawn it retracts the needle into the casing where the pre-stressed condition causes the needle to bow out of alignment with the channel of the cap.

In another embodiment, a housing with spaced apart walls connected together around their peripheries by an annular wall is provided along with a disc movable inside the housing between the spaced apart walls. The disc and spaced apart walls each have an aperture therethrough through which the needle passes before its one time use. When the needle is withdrawn from the housing after use of the syringe, the disc moves within the housing interfering with passage of the needle through the apertures in the housing walls a second time. The disc moves because of gravity or because of a spring provided between the disc and annular wall of the housing.

In still another embodiment, the cap is rotatably mounted on the casing from an injection position to a non-injection or blocking position. When the needle is retracted, the cap is rotated such that the needle is no longer aligned with channel in the cap.

BRIEF DESCRIPTION OF THE DRAWINGS

FIG. 1 is an enlarged elevational, cross sectional view of the preferred embodiment syringe of the present invention.

FIG. 1A is side elevational view of a barrel portion of the syringe of FIG. 1.

FIG. 1B is a side elevational view of a piston rod portion of the syringe of FIG. 1.

FIGS. 3A and 3B are elevational, cross sectional views of the syringe of FIG. 1 with a first alternate embodiment of a needle blocking portion of the syringe shown before and after use of the syringe, respectively.

FIGS. 5A and 5B are elevational, cross sectional views of the syringe of FIG. 1 with a second alternate embodiment of a needle blocking portion of the syringe shown before and after use of the syringe, respectively.

FIG. 10 is an elevational, cross sectional view of the syringe of FIG. 1 with a first alternate embodiment of a needle portion of the syringe.

FIG. 11 is an elevational, cross sectional view of the syringe of FIG. 1 with a second alternate embodiment of a needle portion of the syringe and an alternate embodiment stopper portion of the syringe.

FIG. 12 is an elevational, cross sectional view of the syringe of FIG. 1 with a first alternate embodiment piston assembly.

FIG. 13 is an elevational, cross sectional view of the syringe of FIG. 1 with an alternate embodiment stop cock portion of the syringe.

FIGS. 14A and 14B are enlarged, elevational, cross sectional views of an alternate embodiment of the syringe with a needle blocking portion shown before and after use of the syringe.

DETAILED DESCRIPTION OF THE DRAWINGS

Figure 2A:
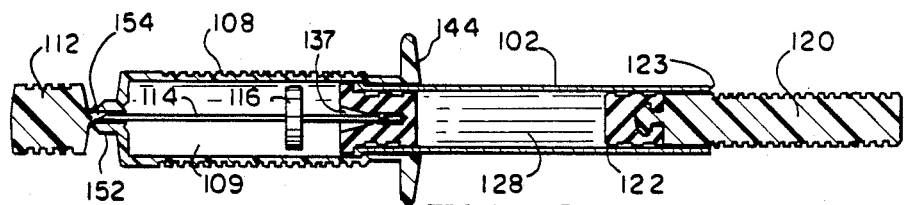
FIGS. 2A through 2F are a series of real size, elevational, cross sectional views of the syringe of FIG. 1 in various stages of use.
Figure 2B:
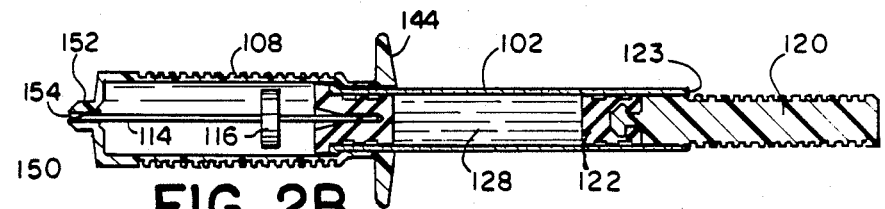

Referring now to FIG. 1, a preferred embodiment syringe designated generally 100 is shown having: a hollow cylindrical body or barrel 102, closed at one end by a stoppper 104 and at the other end by a piston assembly designated generally 106; a hollow cylindrical casing 108 defining a sterile chamber 109 and adapted to receive the stopper 104 and the end of barrel 102 and closed at the other end by a cap 110 with break off tip 112; and a retractile needle 114 with stop cock 116 positioned in the sterile chamber 109 and supported before its intended use at one end by the cap 110 and at its opposite end by the stopper 104.

The piston assembly 106 includes a cylindrical rod 120 and piston 122. The rod and piston are adapted to fit in the end 123 of barrel 102 in sliding engagement with the internal wall thereof. One end of the rod 120 is arrow shaped at 124 for easy assembly with the piston 122. The end 126 of the rod 120 opposite the arrow shaped end 124 is disposed to fit in the end 123 of the barrel 102 when the piston is inserted fully into the barrel 102 to prevent re-use. The liquid 128 to be injected (injectant) is contained within the chamber formed by the barrel 102, the stopper 104 and piston 122. The piston assembly serves as a plunger in a syringe.

The rod may be made of polypropylene or any other suitable material while the piston is made of rubber or plastic and may be covered with Teflon ® (a Dupont trademark for a plastic tetrafluorethylene homopolymer) of other suitable coating to make it compatible with a broad spectrum of substances that might be used as the injectant.

The barrel 102 is preferably made of glass but could be made of other materials compatible with the injectant 128. At the end opposite end 123 the body comprises a bead 132 whose purpose will be described hereinafter. FIG. 1A shows the barrel 102 of FIG. 1 with scale markings 180 shown on the side thereof to provide a measure of the amount of injectant injected. In FIG. 1B, the scale markings 180 are shown on the side of the piston rod 120.

The stopper 104 is preferably made of rubber especially shaped to fit the bead 132 and having a first cylindrical portion 136 adapted to fit within the barrel 102 in sealing engagement with the internal walls thereof and a second larger cylindrical shoulder 138 integrally formed with the first portion and adapted to move within the chamber 109 in sliding engagement with the internal walls of casing 108. The stopper is curved where the first and second portions 136 and 138, respectively, come together to accommodate the inner portion of bead 132. The inner part of the bead 132 holds the stopper in place within the barrel 102 at the time of assembly, during retraction and after use.

Stopper 104 further comprises a funnel shaped elongated channel 137 located coaxially with the axis of the cylindrical stopper and having the larger base of the funnel opening into the chamber 109 to accept one end of the retractile needle 114. The funnel shape helps to position the needle 114 within the channel during assembly of the syringe. In the preferred embodiment, the channel 137 does not pass all the way through the stopper 104, and is thereby isolated from the injectant 128 before use of the syringe 100. The stopper 104 serves to provide a watertight joint between the barrel 102 and the casing 108 at shoulder 138, and to provide support for the retractible needle 114.

The cylindrical casing 108 is preferably made of polypropylene or other suitable material and is open at its distal end opposite stopper 104 but covered by cap 110. The casing 108 has a diameter just smaller than the diameter of the shoulder 138 for most of its length from the distal end, past the shoulder 138 and bead 132 where it narrows slightly at 140 to engage a surface of the outer portion of bead 132. The narrowed portion 142 has a short length of a diameter just larger than the outside diameter of the barrel 102 where it ends in a support ring 144, extending radially outwardly from the barrel 102. The engagement of the narrowed portion 142 with the bead 132 prevents the barrel 102 from slipping out of the casing before and after use. The support ring 144 aids in holding the syringe during injection. Since the shoulder 138 of the rubber stopper is larger then the internal diameter of the casing 108, the rubber is compressed when extending the casing which give a tight fit and good sealing properties.

The cap 110 has an annular wall portion 148 which surrounds the circumferential wall of the distal end of casing 108. Formed integrally with the annular wall portion 148 and extending perpendicularly therefrom, circular wall portion 150, of cap 110 partially closes off the distal end of the casing 108. At the center of the circular wall portion 150, a protrusion 152 is formed extending perpendicularly away from the circular wall portion 150 and the syringe. A channel 154 is formed through the protrusion 152 and is open at one end to accept the tip of retractile needle 114.

The tip 112 is attached to the protrusion 152 at its distal end loosely enough to allow for easy break-off at the time of use. The break off tip 112 keeps the needle sterile and makes it possible to see if the syringe has been used, thus making it tamper-evident. The cap with break-off tip is placed on the casing 108 in final assembly and seals the end of the syringe.

The dispensing tip 160 of needle 114, used for the point of injection, is pointed and standard in shape. At the other end, close to the inside tip 162, is a lateral hole 164 which allows the injectant 128 to flow from the interior of the barrel 102 through the needle at the time of injection. The gauge of the needle 114 at both ends is between 14 and 24.

The stop cock 116 is circular in shape and is attached to the needle 114 and coaxial therewith within the chamber 109. The position of the stop cock 116 along the length of the needle 114 within the chamber 109 is important for proper operation of the syringe and will be discussed in connection therewith. The stop cock 116 may be made of polypropylene or other suitable material and need not be circular in all embodiments.

Referring now to FIGS. 2A through 2F, upon receipt of the syringe 100 by the end user (FIG. 2A) the barrel 102 is filled with injectant 128 and is ready to use. The break off tip 112 is loosely attached to the end of protrusion 152, and the retractile needle 114 is safely contained within the sterile chamber 109 supported at both ends by funnel shaped channel 137 and channel 154 in protrusion 152. The piston rod 120 is withdrawn from the barrel 102 interior with only the piston 122 and a portion of the end of rod 120 within the interior of barrel 102.

Figure 2C:
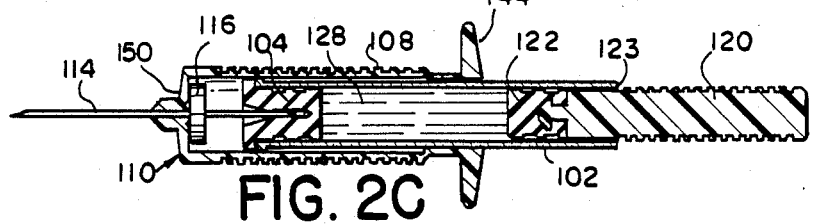
Figure 2D:
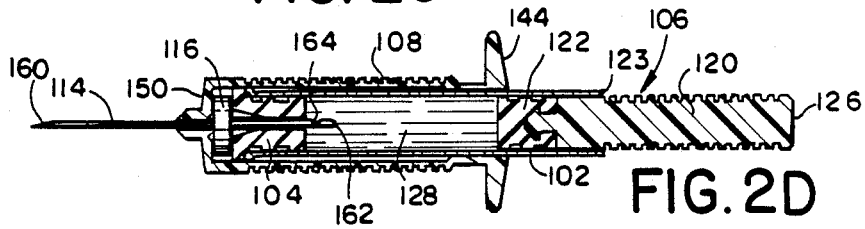

The user first breaks off the tip 112 of FIG. 2A (see FIG. 2B) and then, grabbing the wall of the barrel 102, pushes the body inside the casing 108, which causes the needle 114 to pass through the channel 154 in protrusion 152 until the stop cock 116 engages the circular wall portion 150 of cap 110 (FIG. 2C). (Alternatively, the casing 108 includes a circular end wall having a hole therethrough aligned with the channel 154, and the stop cock engages the casing end wall.) As the barrel 102 is pushed farther into the casing 108 the stop cock 116 holds the needle in place and prevents the needle 114 from extending out through the protrusion 154 any farther causing the tip 162 to puncture the remaining portion of the stopper 104 thereby placing the hole 164 into the injectant 128 (FIG. 2D). The syringe is now ready for injection. Note the barrel 102 is longer than the casing 108, and, when fully inserted into the casing, a portion of the barrel near end 123 extends out beyond ring 144.

Figure 2E:
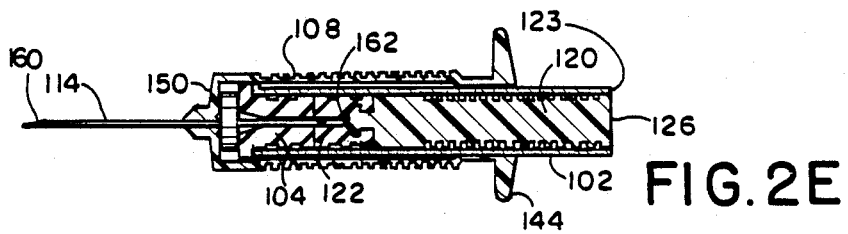

The injection is performed when the user pushes the rod 120 and therefore the piston 122 inside the barrel 102 thus forcing the injectant to flow through hole 164, needle 114 and needle tip 160. The piston assembly 106 is pushed into the barrel until the piston 122 engages the stopper 104 and they are together (FIG. 2E). The inside tip 162 of the needle 114 enters the piston 122 and the injectant is completely and totally injected (FIG. 2E). The end 126 of the rod 120 whose outer diameter matches the inner dimension of the barrel 102 is now inside the barrel 102 preventing its re-use (FIG. 2E).

Figure 2F:
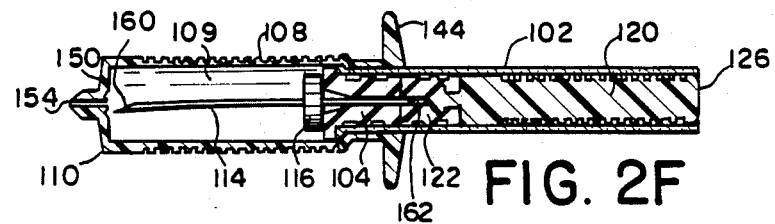

To retract the needle 114, the user pulls the barrel 102 (grabbing hold of the barrel portion left extended beyond ring 144) to withdraw it from within the casing 108 (FIG. 2F). The needle 114 which is now inserted through stopper 104 into piston 122 is withdrawn as well through the channel 154 until the tip 160 is within chamber 109 and clear of the cap 110. When retracted, the needle is slightly off set and non-aligned with channel 154 because, in the preferred embodiment, it was prestressed so that when no longer supported at tip 160 by cap 110 the needle bows within chamber 109. This renders the syringe non-reusable and safer than conventional syringes during subsequent handling.

Total retraction is made possible because, after the stop cock reaches the circular wall portion 150, as the barrel 102 is pushed farther into the casing, the stopper moves along the needle until it engages the stop cock 116. Effectively this shortens the needle 114, so that, when the barrel is withdrawn from the casing, it pulls the needle along with it and the needle is not long enough to reach the cap 110.

The stopper 104, stop cock 116 and the piercing of the piston 122 by the tip 162 of needle 114 cooperate together to provide a means for extending the needle through the end of the casing and placing the needle in fluid communication with the injectant as the barrel is moved forward within the casing and for retracting the needle back into the casing when the barrel is withdrawn from the casing. The cap or end wall, as well as the shortened portion of needle extending beyond the stopper after the injection, cooperate together to provide a means for blocking the needle from extending through the end of the casing substantially closed by the cap or end wall after the needle has been retracted.

Referring now to FIGS. 3A, 3B and 4A, 4B as an alternate blocking means embodiment to the prestressed needle, a straight needle could be used with the needle blocking device designated generally 300. It is shown in side, elevational cross section in FIGS. 3A and 3B and comprises a circular housing having two parallel and spaced apart walls 302 and 304 connected around their perimeter by an annular wall 306. The circular walls 302 and 304 each have a coaxial center hole 307 and 308, respectively.

The blocking device 300 further includes a circular disc 310 disposed between the walls 302 and 304 also having a center hole 312. The disc has a smaller diameter than the circular walls 302 and 304 and is free to move within the housing. During assembly the device is positioned between the open end of the casing 108 and the circular wall 150 of cap 110. The center hole 312 is aligned coaxially within the holes 307 and 308 and the needle 314 is positioned within the casing through the holes 307 and 308 and 312. When the needle is retracted back into the casing after use as described above, the disc 310 falls down within the housing so that the hole 312 is no longer aligned with holes 307 and 308 and it is impossible to extend needle 314 back through channel 154 a second time since the disc 310 will block it. See FIGS. 3B and 4B.

Figure 4A:
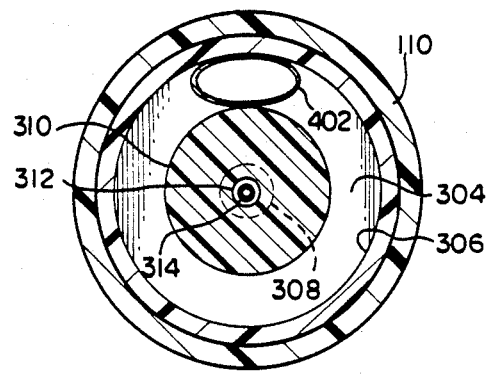
FIGS. 4A and 4B are enlarged, elevational cross sectional views of the needle blocking portion of FIGS. 3A and 3B taken along the lines and arrows 4A and 4B, respectively.
Figure 4B:
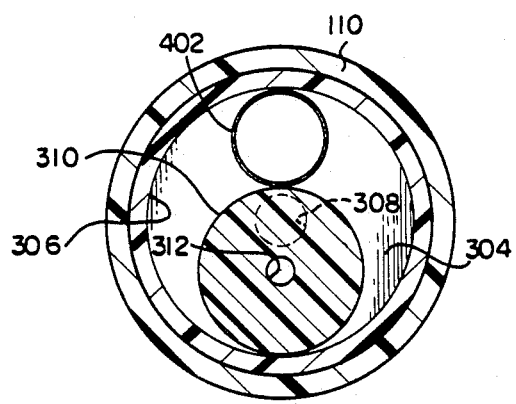

In FIGS. 4A and 4B, a planar elevational view of the device in cross section is shown having an oval spring 402 disposed between the outer perimeter of disc 310 and the inner surface of annular wall 306. In FIG. 4A, needle 314 is shown within the hole 312 which is aligned with the holes in the circular walls 302 and 304 as if in the pre-use position with the spring 402 compressed. When the needle 314 is withdrawn the spring 402 pushes the disc 310 out of alignment with the holes 307 and 308. See FIGS. 3B and 4B.

In FIGS. 5A and 5B, a cap 510 is shown with a protrusion 552 offset from center on the circular wall portion 550 along with the funnel shaped channel 537 in stopper 504. After the needle is retracted after use, the cap 510, which is adapted to be rotated on casing 508, is rotated, as in FIG. 5B, whereby the channel 554 is no longer aligned with the needle 514 and channel 537.

Figure 6:
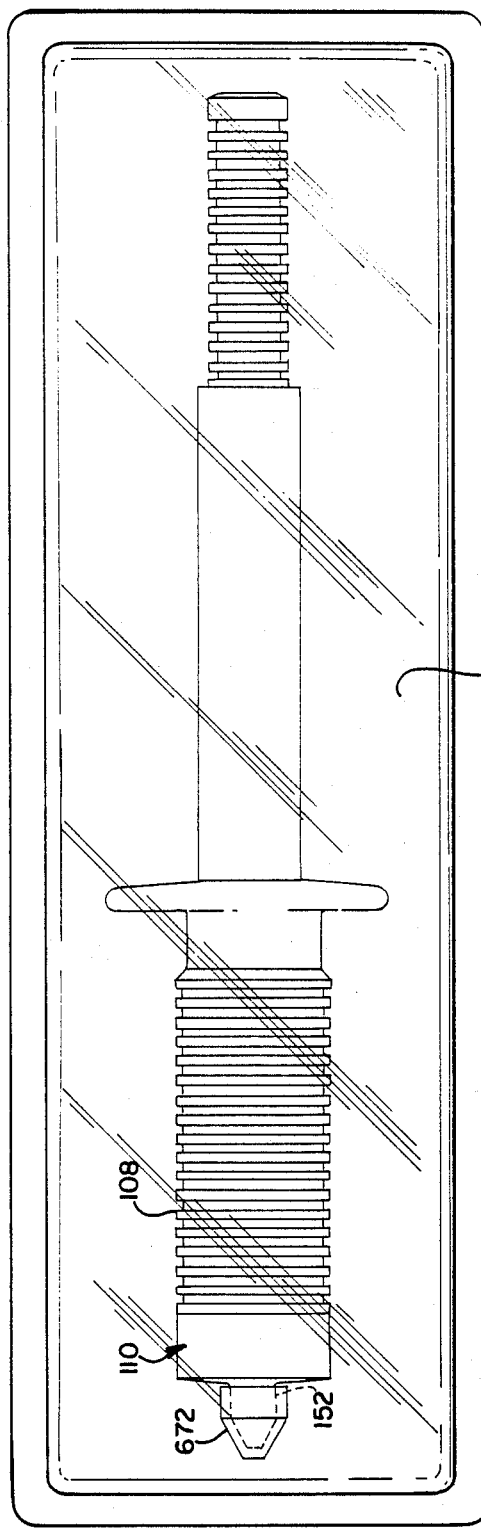
FIG. 6 is an elevational view of the syringe of FIG. 1 with a first alternate embodiment of a cap portion of the syringe.
Figure 7:
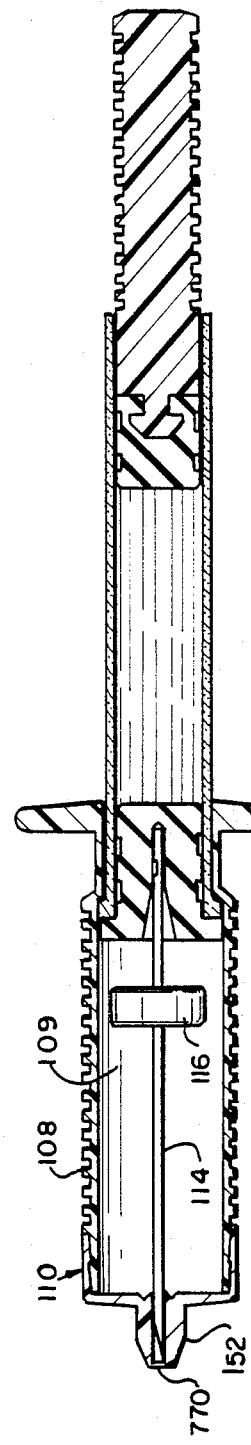
FIG. 7 is an elevational, cross sectional view of the syringe of FIG. 1 with a second alternate embodiment of a cap portion of the syringe.

As FIG. 6 shows, the break off tip 112 of FIG. 1 may be eliminated and the entire syringe placed in a sterile package 670 with the break off tip replaced by a standard cap 672 over the protrusion 152. Alternatively, as shown in FIG. 7, the break off tip 112 of FIG. 1 could be replaced by a thin membrane 770 to be perforated at the time of use.

Figure 8:
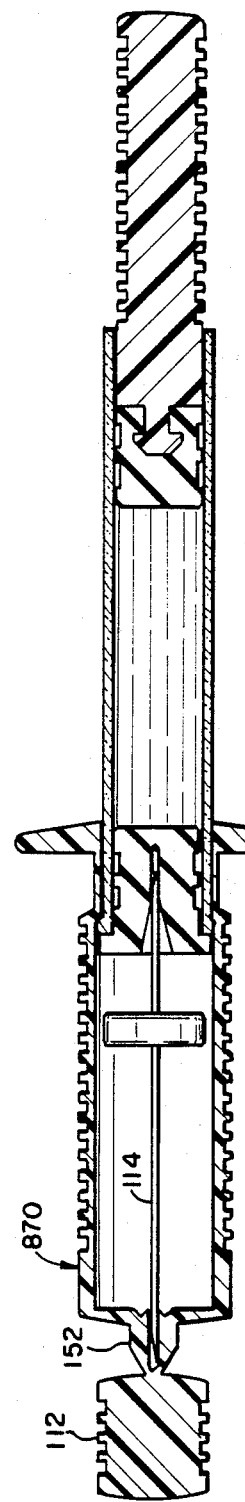
FIG. 8 is an elevational, cross sectional view of the syringe of FIG. 1 with a first alternate embodiment of a casing portion of the syringe shown integrally molded with a cap portion and tip portion of the syringe.

In FIG. 8, the cap 110 of FIG. 1 is shown integrally formed with the casing 108 and break off tip 112 to form a combined casing break-off tip and cap 870.

Figure 9:
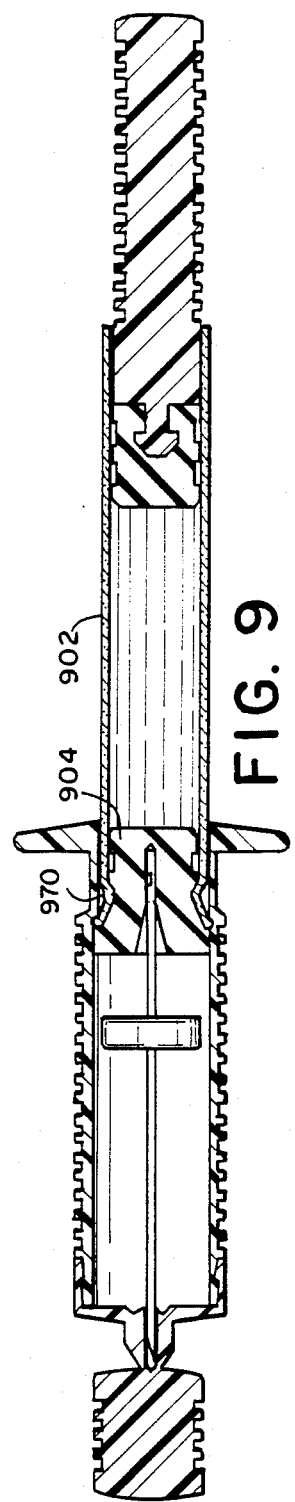
FIG. 9 is an elevational, cross sectional view of the syringe of FIG. 1 with an alternate embodiment barrel portion of the syringe.

FIG. 9 shows an alternate embodiment of the syringe of FIG. 1 wherein the bead 132 at the end of the body 102 in FIG. 1 is replaced with an inwardly directed annular depressed region 970 on barrel 902 which fits into an annular groove in the stopper 904. FIG. 10 shows the inside tip 1062 of the needle 1014 taking the shape of a hook to retain strongly the needle inside the piston 122 after injection. FIG. 10 also shows the lateral hole 164 of FIG. 1 replaced with a circular orifice 1064.

In FIG. 11 the stopper 104 is replaced with a diaphragm 1170 stretched across an opening in the bottom of a cylindrically shaped support member 1172 having an annular radially directed flange 1174 which engages bead 132 of FIG. 1 on body 102. The inside tip 1162 of the needle has a standard shape. When the body 102 is inserted into the casing 108 the tip 1162 will puncture the diaphragm 1170. Stop cock 1116 has a diameter such that the stop cock engages the inside walls of the casing to ensure proper alignment of the needle since there is no longer any support for the needle in a stopper.

In FIG. 12 coupling between rod 1220 and piston 1222 is accomplished by a thread and screw arrangement designated generally 1270.

FIG. 13 shows a modification to the syringe of FIG. 1 wherein a stop cock 1370 is added forward of stop cock 116 to control the length of the needle 114 which extends out beyond the casing 108. For example, when the body 102 is pushed into the casing the stopper pushes the needle 114 forward until stop cock 1370 engages the circular wall portion 150 of the cap. The needle extends out no farther. When the body 102 is pushed farther, the tip 162 of the needle 114 will penetrate the stopper 104 as the stopper reaches stop cock 116 positioning the opening 164 in the injectant 128.

The alternate embodiment features discussed above in connection with FIGS. 6 through 13 are applicable to the pre-stressed needle embodiment of FIG. 1, the straight needle and blocking device of FIGS. 3A and 3B, and, except for the integral combination of FIG. 8, the rotatable cap embodiment of FIGS. 5A and 5B.

Referring now to FIGS. 14A and 14B, an alternate embodiment retractile needle syringe designated generally 1400 comprises a conventional syringe designated generally 1401 having a barrel portion 1402 for holding the injectant, a piston assembly 1406 with rod 1420 and piston (not shown) within barrel 1402 and a needle 1414. The needle is held rigid to barrel 1402 by a body collar 1470 which also serves to seal the barrel 1402.

The syringe 1400 further includes a casing 1408 into which the barrel collar 1470 and a portion of barrel 1402 is inserted during assembly; a cap 1410 similar to the cap 110 in FIG. 1; and a needle blocking device 1480 identical to the device 300 described in FIGS. 3A, 3B and 4A, 4B. The syringe 1400 also has a break off tip 1412.

In FIG. 14A before the syringe 1400 is used, the barrel 1402 and collar 1470 are shown positioned within casing 1408 with the collar 1470 spaced apart from end 1472 of the casing by the annular protrusion 1474 which is the preferred embodiment is a small molded protrusion in the interior of the casing 1408.

The syringe 1400 is used in a manner as described earlier in connection with FIG. 1. The break off tip 1412 is removed, the barrel 1402 inserted into the casing 1408 until the collar 1470 contacts the blocking device 1480. Then the piston rod 1420 is pressed into the barrel 1402. After injection, the barrel is withdrawn from the casing pulling the collar past the annular projection 1474 until the disc 1482 within the needle blocking device 1480 covers the opening in the housing and the syringe is prevented from being reused. The collar will move past the protrusion 1474 since it is only a small molded piece and will give way if a modest pulling force is exerted on the barrel 1402.

Assembly of the preferred embodiment syringe is accomplished as follows: First, the piston 122 is snapped into place around the arrow shaped protrusion 124 of piston rod 120. Then the plunger assembly 106 thus formed is partially entered into the barrel 102, piston first. Next, the entire assembly is inserted into the casing 108 and the barrel 102 filled with injectant 128. The stopper 104 is placed into the barrel to secure the injectant and the tip 162 of needle 114 is placed into the stopper channel 137. The opposite end 160 of the needle is placed into the cap protrusion channel 154 and the casing 108 pulled up around the needle to be coupled to the cap 110. The syringe is now ready for use.

The present invention syringe provides a number of important benefits to the end user. The syringe with retractile needle can be discarded with no fear of causing injuries with the sharp tip of the needle. The break-off tip on the cap makes it easy to see if the syringe has already been used. The needle is kept in the sterile surrounding wall and emerges only at the time of use, and the liquid comes in contact with the needle only at the time of injection. The syringe is easy to use in three operations: break off the tip; insert the body into the casing; and inject the injectant.

From a manufacturing point of view, the piston and stopper can be coated with Teflon ® material or any other suitable coating to allow compatibility with a broad spectrum of substances. The syringe is easily assembled and stored. Costly individual packaging is eliminated.

What is claimed is:

1. An apparatus for a one time injection of a liquid injectant comprising:
   a hollow cylindrical casing having a first open end and a second opposite end;
   a barrel for holding said injectant, said barrel disposed at a first end to slide through said first open end of said casing from a remote pre-injection position to a forward injection position and back again;
   means coupled to said barrel for ejecting said injectant;
   a hollow needle disposed within said casing and having an opening at each end thereof;
   means for extending said needle through said casing second end and placing said needle in fluid communication with said injectant when said barrel moves from said remote pre-injection position to said forward injection position and for retracting said needle through said casing second end into said casing when said barrel moves back again to said pre-injection position; and
   means for blocking automatically said needle from extending through said casing second end after said needle has been retracted.

2. The apparatus of claim 1 wherein said needle blocking means comprises:
   a planar housing with parallel and spaced apart walls attached along their periphery by an annular wall, said housing perpendicular to said needle, each of said walls having an opening lying along a common axis;
   a disc disposed within said housing between said planar walls, said disc having an aperture therethrough, said disc movable within said housing between a position wherein said aperture is aligned with the openings in said planar walls and a position wherein the aperture is non-aligned with the openings in said planar walls, said needle located through said planar wall openings and said disc aperture before said single use, and withdrawn from said apertures after retraction.

3. The apparatus of claim 2 wherein said needle blocking means further comprises:
a spring located between said disc and said annular wall for biasing said disc into said non-alignment position.

4. The apparatus of claim 1 wherein said extending and retracting means comprises:
means for engaging said needle to extend said needle through said casing second end when said barrel moves to said forward injection position; and
a first stop cock fixed to said needle intermediate said second end of said casing and said engaging means at a predetermined distance from said casing second end such that, when said barrel moves from said remote pre-injection position to said injection position, said stop cock engages said second end of said casing and said engaging means engages said stop cock to force said second end of said needle through said stopper into fluid communication with said injectant.

5. The apparatus of claim 4 wherein said apparatus further comprises:
a second stop cock fixed to said needle intermediate said first stop cock and said second end of said casing for controlling the length of extension of said needle through said casing second end.

6. The apparatus of claim 4 wherein said engaging means comprises a stopper inserted in said first end of said barrel having a channel open at a first end to receive a first end of said needle, said channel closed at its opposite end to prevent contact between said injectant and said needle before said one time injection.

7. The apparatus of claim 6 wherein said opening at said first end of said needle is a lateral opening spaced apart from the tip of said needle.

8. The apparatus of claim 7 wherein said needle comprises a hook located at the tip of said first end of said needle.

9. The apparatus of claim 4 wherein said engaging means comprises a diaphragm means stretched across said first end of said barrel for separating said injectant from said needle.

10. The apparatus of claim 1 wherein said apparatus further comprises a cap coupled to said second end of said casing, said cap having a protrusion extending axially outwardly from said second end of said casing and a channel through said protrusion opening into the hollow interior of casing at one end, said protrusion, channel disposed to receive said needle as it is extended through said casing second end.

11. The apparatus of claim 10 wherein said cap further comprises a break-off tip which closes off said channel in said protrusion, said break-off tip adapted to be broken off to open said channel to ambient atmosphere.

12. The apparatus of claim 11 wherein said cap, break-off tip and said casing are integrally formed.

13. The apparatus of claim 10 wherein said blocking means comprises:
said cap rotatably mounted to said second end of said casing and rotatable from an injection position to a non-injection position, said channel through said protrusion disposed to receive said needle only in said injection position.

14. The apparatus of claim 1 wherein said ejecting means comprises a plunger disposed to enter an open second end of said barrel opposite said casing.

15. The apparatus of claim 14 wherein said plunger further comprises a piston rod coupled at a first end to a piston adapted for sliding and sealing engagement with the interior wall of said barrel, the end of said piston rod opposite said first end and the length of said piston rod being such that substantially all of said piston rod including said second end fits snugly within said barrel after the injection.

16. The apparatus of claim 1 wherein said blocking means comprises:
a pre-stressed needle; and
means for preventing extension of said pre-stressed needle through said casing second end when said needle is in a stressed position after retraction.

17. The apparatus of claim 16 wherein said needle extension preventing means comprises:
an opening in a wall portion closing off said casing second end.

18. The apparatus of claim 16 wherein said extension preventing means comprises:
a cap coupled to said second end of said casing, said cap having a protrusion extending axially outwardly from said second end of said casing and a channel through said protrusion opening into the hollow interior of said casing at one end, said protrusion receiving said needle at said at one end of said protrusion before the one time injection, but unable to receive said needle after retraction because of said pre-stressing.

19. The apparatus of claims 10, 13 or 18 wherein said extending and retracting means further comprises a stopper inserted in said first end of said barrel having a channel open at a first end to receive a first end of said needle opposite the end of said needle disposed within said protrusion channel.

20. The apparatus of claim 19 wherein said cap further comprises a break-off tip which closes off said channel in said protrusion, said break-off tip adapted to be broken off to open said channel to ambient atmosphere.

21. The apparatus of claim 20 wherein said cap, break-off tip and said casing are integrally formed.

22. The apparatus of claims 2, 10, 13, or 16 wherein said extending and retracting means comprises:
a first stop cock fixed to said needle intermediate said second end of said casing and said engaging means at a predetermined distance from said casing second end such that, when said barrel moves from said remote pre-injection position to said injection position, said stop cock engages said second end of said casing and said engaging means engages said stop cock to force said second end of said needle through said stopper into fluid communication with said injectant.

23. The apparatus of claim 22 wherein said apparatus further comprises:
a second stop cock fixed to said needle intermediate said first stop cock and said second end of said casing for controlling the length of extension of said needle through said casing second end.

24. The apparatus of claims 2, 13, or 16 wherein said opening at said first end of said needle is a lateral opening spaced apart from the tip of said needle.

25. The apparatus of claims 2, 13, or 16 wherein said needle comprises a hook located at the tip of said first end of said needle.

26. The apparatus of claims 1, 2, 13 or 16 wherein said barrel comprises scale markings on the outside surface thereof whereby the amount of injectant ejected from said barrel can be monitored.

27. The apparatus of claim 15 wherein said piston rod and piston are coupled together by a thread and screw arrangement.

28. The apparatus of claims 1, 2 or 3 wherein said extending and retracting means comprises a collar for rigidly attaching said needle to said first end of said barrel.

29. The apparatus of claim 28 wherein said apparatus further comprises means for positioning an injection end of said needle at a forward pre-injection position within said casing.

30. The apparatus of claim 29 wherein said positioning means comprises a protrusion within said casing interior intermediate said collar and the first end of said casing.

* * * * *